(12) United States Patent
Scharmer et al.

(10) Patent No.: US 10,688,269 B2
(45) Date of Patent: Jun. 23, 2020

(54) GAS SENSOR FOR ANESTHETIC GASES AND ITS USE

(71) Applicant: Drägerwerk AG & Co. KGaA, Lübeck (DE)

(72) Inventors: Ernst-Günter Scharmer, Krummesse (DE); Wolfgang Bäther, Lübeck (DE); Livio Fornasiero, Bliestorf (DE); Christoph Marquardt, Stockelsdorf (DE); Günter Steppan, Bad Oldesloe (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 367 days.

(21) Appl. No.: 15/484,226

(22) Filed: Apr. 11, 2017

(65) Prior Publication Data

US 2017/0296771 A1   Oct. 19, 2017

(30) Foreign Application Priority Data

Apr. 13, 2016   (DE) .......................... 10 2016 004 338

(51) Int. Cl.
*A61M 16/10*   (2006.01)
*G01N 27/414*   (2006.01)
(Continued)

(52) U.S. Cl.
CPC .... *A61M 16/1005* (2014.02); *A61M 16/0093* (2014.02); *A61M 16/01* (2013.01);
(Continued)

(58) Field of Classification Search
CPC ............ A61M 16/009; A61M 16/0093; A61M 16/01; A61M 16/0891; A61M 2016/1035; A61M 2202/0241; A61M 16/00; A61M 16/0003; A61M 16/1005; A61M 16/105; A61M 16/1075; A61M 16/18; A61M 16/208; A61M 16/209; A61M 16/22; H01L 27/0629; G01N 27/125; G01N 27/4141

See application file for complete search history.

(56) References Cited

U.S. PATENT DOCUMENTS

| | | | |
|---|---|---|---|
| 4,411,741 A | 10/1983 | Janata | |
| 2006/0006470 A1* | 1/2006 | Harada | ............... H01L 27/0629 257/351 |

(Continued)

FOREIGN PATENT DOCUMENTS

| | | |
|---|---|---|
| DE | 66 00 383 U | 1/1969 |
| DE | 43 33 875 C2 | 8/1995 |

(Continued)

OTHER PUBLICATIONS

I. Lundström, S. Shivaraman, C. Svensson and L. Lundkvist, A hydrogen-sensitive MOS field effect transistor, Appl. Phys. Lett. 26, 55 (1975).

(Continued)

*Primary Examiner* — Joseph D. Boecker
(74) *Attorney, Agent, or Firm* — McGlew and Tuttle, P.C.

(57) ABSTRACT

A gas sensor for the detection of gases and vapors in air is particularly for the detection of anesthetic gases. A method for the detection and for the monitoring of such gases is also provided including detecting anesthetic gases with the gas sensor.

20 Claims, 9 Drawing Sheets

(51) Int. Cl.
*A61M 16/00* (2006.01)
*A61M 16/08* (2006.01)
*A61M 16/01* (2006.01)
*A61M 16/20* (2006.01)
*G01N 27/12* (2006.01)
*H01L 27/06* (2006.01)
*A61M 16/22* (2006.01)
*A61M 16/18* (2006.01)

(52) U.S. Cl.
CPC ...... *A61M 16/0891* (2014.02); *A61M 16/105* (2013.01); *A61M 16/1075* (2013.01); *A61M 16/208* (2013.01); *G01N 27/125* (2013.01); *G01N 27/4141* (2013.01); *H01L 27/0629* (2013.01); *A61M 16/18* (2013.01); *A61M 16/209* (2014.02); *A61M 16/22* (2013.01); *A61M 2016/1035* (2013.01); *A61M 2202/0241* (2013.01); *A61M 2205/581* (2013.01); *A61M 2205/583* (2013.01); *A61M 2209/10* (2013.01)

(56) References Cited

U.S. PATENT DOCUMENTS

| | | | | |
|---|---|---|---|---|
| 2007/0189931 A1* | 8/2007 | Ruhe | ................ | G01N 33/0059 422/88 |
| 2009/0078026 A1* | 3/2009 | Wilbertz | ............ | G01N 27/4143 73/31.06 |
| 2009/0246084 A1* | 10/2009 | Wilbertz | ............ | G01N 27/4143 422/98 |
| 2011/0146382 A1* | 6/2011 | Fleischer | ............ | G01N 27/4143 73/25.01 |
| 2013/0126947 A1* | 5/2013 | Wilbertz | ................ | H01L 29/66 257/253 |
| 2013/0139570 A1* | 6/2013 | Senft | ...................... | H01L 29/66 73/31.06 |
| 2013/0211207 A1* | 8/2013 | Joseph | ................ | A61M 16/104 600/301 |
| 2014/0361901 A1* | 12/2014 | Hoefer | ................ | G08B 29/188 340/628 |
| 2015/0059744 A1* | 3/2015 | Fisher | ................ | A61M 16/024 128/203.14 |
| 2016/0153882 A1* | 6/2016 | White | ................ | G01N 27/4141 73/29.03 |
| 2017/0168000 A1* | 6/2017 | Ichiki | ...................... | H01L 21/28 |
| 2017/0315083 A1* | 11/2017 | Bather | ............... | G01N 33/0047 |

FOREIGN PATENT DOCUMENTS

| | | |
|---|---|---|
| DE | 10 2005 033 226 A1 | 1/2007 |
| DE | 10 2011 075 396 A1 | 11/2012 |
| DE | 10 2014 000 343 A1 | 7/2015 |
| DE | 10 2014 016 394 A1 | 5/2016 |
| EP | 2 006 668 A1 | 12/2008 |

OTHER PUBLICATIONS

COERS: Systematik der Anästhesiebeatmungsgeräte, Mar. 2005, pp. 1-32.

* cited by examiner

FIG. 1

FIG. 2 State of the Art

GAS SENSOR FOR ANESTHETIC GASES AND ITS USE

CROSS REFERENCE TO RELATED APPLICATIONS

This application claims the benefit of priority under 35 U.S.C. § 119 of German Application 10 2016 004 338.5, filed Apr. 13, 2016, the entire contents of which are incorporated herein by reference.

FIELD OF THE INVENTION

The present invention pertains to a gas sensor for detecting gases and vapors in air, especially anesthetic gases; to a method for detecting and for monitoring such gases, and to the use of the gas sensor.

BACKGROUND OF THE INVENTION

Commercially available anesthesia devices make available an exactly defined anesthetic gas concentration in the breath of a patient. Prior-art anesthetic gases are, e.g., sevoflurane, desflurane, isoflurane, enflurane and halothane. Oxygen, laughing gas or compressed air are used as carrier gases. The anesthesia device is configured, as a rule, as a closed-circuit ventilation system, whose lines are closed into a closed circuit, so that the exhaled air containing anesthetic gas or vapors is again inhaled after passing through a $CO_2$ absorber and corresponding valves. The use of a half-closed closed-circuit ventilation system is, as a rule, preferred, so that the quantity of admitted gas exceeding the effective consumption can escape via a pressure relief valve. A certain anesthetic gas concentration, which is detected and monitored by an anesthetic gas sensor, is to be set to switch off the patient's consciousness and pain sensation. Anesthetic gas is correspondingly dispensed into the closed circuit via an anesthetic evaporator.

Anesthetic gas sensors were proposed, which are based on greatly different principles of measurement. The anesthetic gas monitor according to DE 6600383 U is based, e.g., on the change in the elasticity of a silicone rubber band, caused by the interaction with the anesthetic gas. Other methods are based on spectroscopic or spectrometric methods with the use of mass spectrometers, infrared or Raman spectroscopes, photoacoustics and piezoelectric crystal systems, where infrared spectroscopy has attained special economic significance. However, the relatively high cost of the analyzers is common to the spectroscopic gas-measuring technologies.

The anesthetic gases are, as a rule, chemically inert and at least chemically inactive. Chemical sensors are less suitable for this reason. Consuming sensors have the drawback of having a short service life, especially at relatively high concentrations (e.g., in the vol. % range in which, e.g., anesthetic gases occur).

Gas sensors with receptor surfaces on which the work function of an analyte changes as a function of the analyte concentration are of interest. Chemical reactions do not usually take place in the process.

A chemical field-effective transistor is a special form of a field-effect transistor (FET), which is used as a sensor for chemicals. The design of such a sensor essentially corresponds to that of an insulated-gate field-effect transistor (IGFET), which also includes the prior-art MOSFET, in which the conductive (usually metallic) gate electrode is removed and replaced with a receptor layer. The substances to be detected can preferably be adsorbed on the receptor layer. This can result in a concentration-dependent change in the electrical potential on the boundary surface, which causes a change in the electrical conductivity of the semiconducting channel located under the insulation layer analogously to the applied potential in conventional FETs.

Depending on the functionalization of the receptor layer, such a sensor can be used to detect atoms, molecules and ions in liquids and in the gases. Such sensors for gas analysis were first presented by Lundström in the 1970s (I. Lundstrom, S. Shivaraman, C. Svensson and L. Lundkvist, A hydrogen-sensitive MOS field effect transistor, Appl. Phys. Lett. 26, 55 (1975)). A MOSFET with a "palladium gate" electrode was used to detect hydrogen in these studies. Hydrogen is absorbed atomically by the palladium receptor layer, and a dipole layer, which is at equilibrium with the gas chemisorbed on the surface, is formed in the receptor layer.

A markedly greater variety of receptors and higher accuracy is possible with sensors in which the receptor layer and the FET are separated by an air gap and a reference electrode is used, as it is disclosed in U.S. Pat. No. 4,411,741 and EP 2006668 A1. A corresponding sensor, in which the air gap and the field-effect transistor are separated from one another in space by a gas-sensitive layer, is described in DE 4333875 C2. Such sensors are called suspended-gate sensors (SGFET). The receptor layers used in the above-described SGFET consist essentially of doped metals and compounds thereof. MOFs (metal organic frameworks) are proposed as the receptor in DE 102011075396 A1. EP 2006668 A1 proposes as the coating a monomolecular layer, which contains a silane with organic radical groups.

If the SGFET gas sensor is integrated in a standard MOSFET in the CCFET (Capacitively Coupled Field Effect Transistor) variant, the principle of function is based on the measurement of the change in the work function of a specific analyte molecule. The reaction of the receptor layer is capacitively coupled via the air gap with a subjacent MOSFET, whose channel conductivity is correspondingly modulated. A CCFET gas sensor thus comprises, in principle, an active MOSFET and a passive chip, the suspended gate, which is mounted as a carrier of the receptor layer on the MOSFET. The analyte molecule in the gas to which the CCFET sensor is sensitive is determined by the selection of the receptor layer.

SUMMARY OF THE INVENTION

An object of the present invention is to provide a CCFET sensor for detecting anesthetic gases, which is easy to handle, cost-effective and reliable, by selecting a suitable receptor layer.

According to the invention, a capacitively coupled field effect transistor sensor is provided comprising a receptor layer, an insulation layer, a substrate, a drain, a source, a channel area located between the drain and the source, a gate electrode and a sensor electrode. The channel area is in connection in space with the gate electrode and at least the drain. The source and the channel area are arranged within the substrate. The gate electrode is connected electrically conductively to the sensor electrode. An air gap is present between the sensor electrode and the receptor layer. The sensor electrode and the receptor layer are otherwise separated by the insulation layer. An analyte gas flows through the air gap. The analyte gas is an anesthetic gas and the receptor layer contains positive charge centers.

The CCFET sensor according to the present invention has the following design: The sensor comprises at least two components: The first component comprises the substrate, insulator, sensor electrode and gate electrode, and the second component comprises the carrier element with the carrier layer arranged on the carrier element and a receptor layer likewise arranged on the carrier layer. There is an air gap between the first and second components. The sensor electrode and the receptor layer are located opposite each other, separated by an air gap. The analyte-specific second component is placed on the first component.

The sensor according to the present invention can be used for anesthetic gases that have permanent dipoles. Suitable anesthetic gases have at least one trifluoromethyl group and are, e.g., sevoflurane (1,1,1,3,3,3-hexafluoro-2-(fluoromethoxy)propane), isoflurane ((RS)-difluoromethoxy-1-chloro-2,2,2-trifluoroethane), enflurane ((RS)-2-chloro-1-difluoromethoxy-1,1,2-trifluoroethane), desflurane ((RS)-2-(difluoromethoxy)-1,1,1,2-tetrafluoroethane) and halothane (2-bromo-2-chloro-1,1,1-trifluoroethane). The negative partial charges are located on the fluorine atoms and especially at the oxygen atoms (if present), and the positive partial charges are located on the carbon atoms. The negative charge is distributed in a relatively wide range in trifluoromethyl groups, so that these groups can be considered to be soft Lewis bases. These groups interact according to the HSAB ("hard and soft acids and bases" according to Pearson) principle preferably with soft Lewis acids. Soft Lewis acids are bound into the layer according to the present invention.

Hard Lewis acids are characterized by a small extension in space and positive charge, and they have, as a rule, no non-binding valency electrons. Examples of hard Lewis acids are $H^+$, $Li^+$, $K^+$, $Be^{2+}$, $Mg^{2+}$, $Ca^{2+}$, $B^{3+}$, $Al^{3+}$, $Sc^{3+}$, $C^{4+}$, $Si^{4+}$, and $Ti^{4+}$. Soft Lewis acids are characterized by a great extension in space, by a low positive charge and by polarizability as well as by free valency electrons. Examples of soft Lewis acids are $Ti^+$, $Ni^{2+}$, $Pd^{2+}$, $Pt^{2+}$, $Cu^+$, $Cu^{2+}$, $Ag^+$, $Au^+$, $Zn^{2+}$, $Cd^{2+}$, $Hg^{2+}$, $In^{3+}$, $Ti^{3+}$, $Ge^{2+}$, $Sn^{2+}$, and $Pb^{2+}$. They can be implemented into a semiconductor, e.g., by p-doping.

The use of receptor layers consisting of titanium nitride (TiN with Ti in the oxidation state 3) with a percentage of $Ti^+$ as a dopant or receptor layers consisting of copper phthalocyanine with a percentage of $Cu^{2+}$ as a coating or a combination thereof proved to be especially advantageous.

The anesthetic gases used according to the present invention have a plurality of negative partial charges within one molecule and can therefore act as polydentate ligands. Several weak interaction areas lead to a sufficiently strong interaction, i.e., there is, in the end result, an interaction, which allows the molecule to remain at or near the surface for a sufficiently long time, even in case of a relatively great distance of the anesthetic gas molecule from the surface.

However, the adsorption of the analyte molecules on the surface alone is not yet sufficient, as a rule, for causing a change in the potential between the sensor electrode and the receptor layer. The dipole sums of the adsorbed molecules are preferably anisotropic, i.e., all are oriented possibly in the same direction. Sufficiently large electrical double layers will now build up. Polydentate analytes are especially suitable for obtaining an anisotropic orientation. The molecule is fixed at a plurality of points and thus positioned by supramolecular interactions.

An advantage of the sensors according to the present invention is that these are non-consuming sensors. The principle of measurement is based on (anisotropic) adsorption and desorption; chemical reactions do not take place. This also offers the advantage of an extensive matrix independence, i.e., an extensive independence from the oxygen concentration. Another advantage is the short response time in the range of a few seconds as well as the short recovery time (likewise in the range of seconds). Both are linked with the relatively great distance between the analyte and the receptor (here the Lewis acid): Molecules can be readily adsorbed, but also rapidly desorbed again. Furthermore, the sensors have a high degree of independence from overflow. Adsorbed molecules can leave the surface again relatively easily even at relatively low temperatures. This leads to short recovery times.

The sensors have a nonlinear calibration curve. The resolution is accordingly higher at lower concentrations than at higher concentrations. To obtain better dynamics of the measurement range, two sensors having different sensitivities, e.g., on the one hand, the titanium nitride layer containing a percentage of $Ti^+$, and the copper phthalocyanine layer containing a percentage of $Cu^{2+}$, on the other hand, are used simultaneously, i.e., the same gas stream flows through two different sensors.

The magnitude of the measurement effect, here, the change in the work function, depends, besides on the quantity of the analyte molecules adsorbed on the surface, especially on the permanent dipole moment and the angle of these molecules relative to the normal to the electrode surfaces. The higher the permanent dipole and the smaller the angles relative to the normal, the greater is the measurement effect.

The sensor according to the present invention can measure the anesthetic gas concentration quantitatively in the vol. % range and below, e.g.,

| | |
|---|---|
| Sevoflurane | 0.1-8 vol. %; |
| Isoflurane | 0.2-2 vol. %; |
| Enflurane | 0.2-5 vol. % |
| Desflurane | 2-18 vol. %; and |
| Halothane | 0.3-1.5 vol. %, | and is not influenced, unlike in the case of, e.g., semiconductor-based resistor sensors, by varying oxygen concentrations; it has a very low power consumption and can be rapidly regenerated even after the action of very high analyte concentrations (e.g., after a filter change).

When combining different CCFET sensors with one another in an array and taking into account the respective measurement results, the respective analytes can also be identified if all relevant and possible constituents are known and this has been taken into account in the calibration of the sensor array. It is possible, e.g., to identify whether the desired anesthetic gas is, indeed, still being used. Such a detection offers additional safety.

If no indicator, which indicates the foreseeable end of the filter effect ("end-of-service-life" indicator), is used for the filter, volatile substances potentially occurring in a medical environment may act on the sensor. Such undesired gases may be, for example, formaldehyde, methyl alcohol, ethyl alcohol, isopropyl alcohol, m-xylene, methyl methacrylate, hydrogen peroxide, ethylene oxide, carbon dioxide and laughing gas. A nonreturn valve may be provided in the closed ventilation circuit as a protection against diffusion in order to prevent these gases from contaminating the sensor during non-use.

In addition or as an alternative, the CCFET sensor may be cleaned thermally prior to operation. Heating of the receptor layer to at least 70° C. over a few minutes (e.g., 1 minute to 5 minutes) is sufficient for this. Heating under reduced pressure (e.g., below 500 mbar, preferably below 100 mbar), as is described in DE 102014000343, is useful if accompanying substances with low volatility are present.

The sensors according to the present invention may also be used as a part of a filter depletion indicator, with which an optical and/or acoustic display may be associated, which indicates when the filter capacity is depleted and the filter must be replaced.

The present invention will be explained below as an example based on the following figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
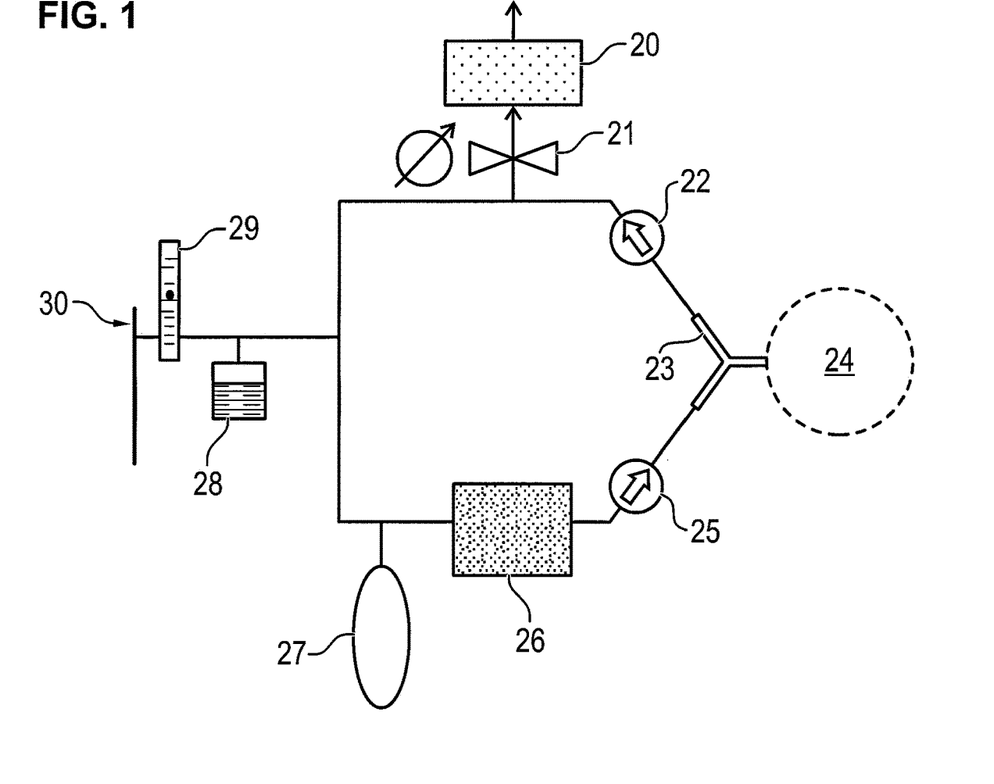
FIG. 1 is a schematic view showing the basic design of an anesthesia device in the form of a closed-circuit ventilation system.

Referring to the drawings, FIG. 1 shows the principle of a closed-circuit ventilation system with anesthesia device, in which the essential components are the directional valves (inhalation valve 25, exhalation valve 22), the $CO_2$ absorber 26, the breathing bag 27, the outlet valve 21, which is configured as a pressure relief valve, folded tubes and the Y-piece 23. If no gas exhaust system is installed in the building, a gas outlet filter 20 is used, as a rule, which binds at least the anesthetic gas. In addition, there is an anesthetic evaporator 28. The carrier gases 30 (e.g., laughing gas, oxygen and/or compressed air) are made available via a gas cylinder-based high-pressure system. The respective carrier gas mixture is set by means of flow meters (29) as a function of the corresponding purpose of anesthesia to which the patient is subjected. The carrier gas mixture (30) is sent through the anesthetic evaporator (28) and thus mixed with the anesthetic gas. The evaporators are calibrated (e.g., compensated for temperature, flow and/or pressure) and coded for a certain anesthetic. The concentration that is relevant here for the anesthesia of a test subject is the so-called minimal alveolar concentration (MAC).

In this case, 1 MAC is the alveolar concentration of an inhaled anesthetic gas in vol. %, which prevents, in the absence of other anesthetics and at equilibrium, 50% of the patients from responding to a normal surgical stimulus with motion (DIN EN ISO 21647). The adequate depth of anesthesia is at 1.2 to 1.4 MAC. This leads ultimately to anesthesia gas concentrations of 1 vol. % to 18 vol. %. The patient 24 inhales the respective carrier gas 30 plus anesthetic gas mixture 28 via the Y-piece 23 and the inhalation valve 25. During the subsequent exhalation, the exhaled air enters the closed circuit via the exhalation valve 22 and finally enters the $CO_2$ adsorber. The carbon dioxide ($CO_2$) reacts there with, e.g., calcium hydroxide to form calcium carbonate and water and is thus removed from the gas circulation. The anesthetic gas mixture present (carrier gas and anesthetic gas(es)) leaves the closed system via the pressure relief valve 21 and enters the operating room after flowing through the filter 20 and via an anesthetic gas discharge line into the exhaust air (not shown). Anesthetic gas sensors may be installed both within the closed-circuit ventilation system, e.g., in the Y-piece 23, but also outside, e.g., after the gas outlet filter. Excess breathing air and hence also the anesthetic gases are discharged to the outside and thus also the operating room via the outlet valve 21. For example, an activated carbon filter 20 is used for absorbing the anesthetic vapors to prevent this. The filter is a consumable part. If the filter is loaded, it must be replaced. The sensor, which shall indicate the breakthrough through the filter 20, is installed downstream directly after the filter 20.

Figure 2:
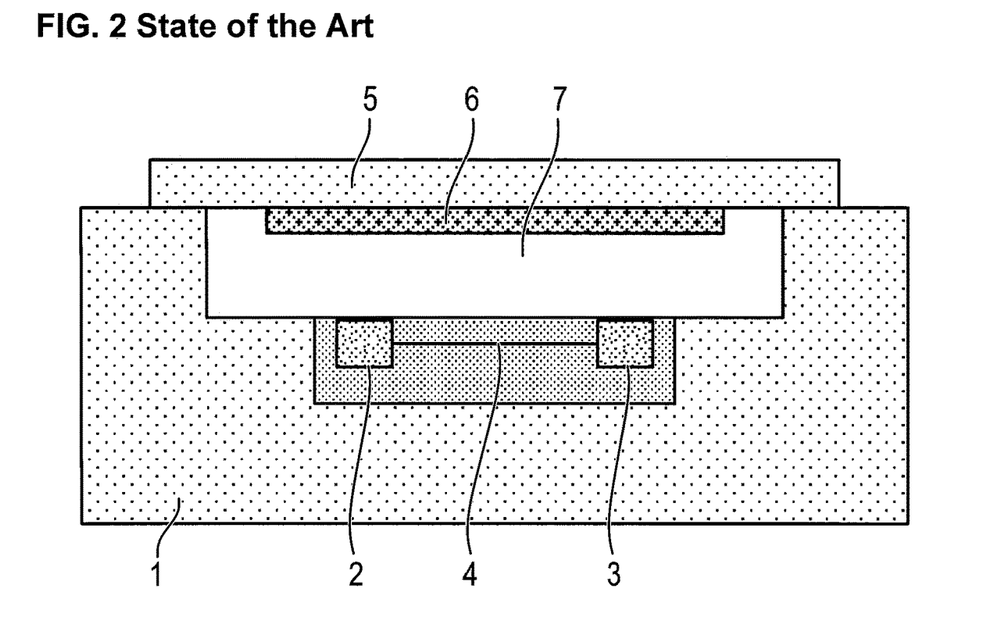
FIG. 2 is a schematic view showing the design of prior-art SG-FET sensors.

A Prior-art suspended-gate sensor (SG-FET) is shown in FIG. 2. The substrate 1 carries here a transistor trough with drain 2 and source 3 and a channel area 4. The cover 5 with the receptor layer 6 is separated from the transistor trough by an air gap 7. The surface of the receptor layer 6 and the channel area 4 are capacitively coupled with one another. The air to be tested reaches the receptor surface via the air gap 7. A reversible change occurs in the work function due to the gas adsorption/surface reaction of the analyte molecules at the receptor layer 6 as a function of the concentration of these molecules. This potential difference couples capacitively via the air gap to the channel surface and induces charges in the FET structure.

Figure 3:
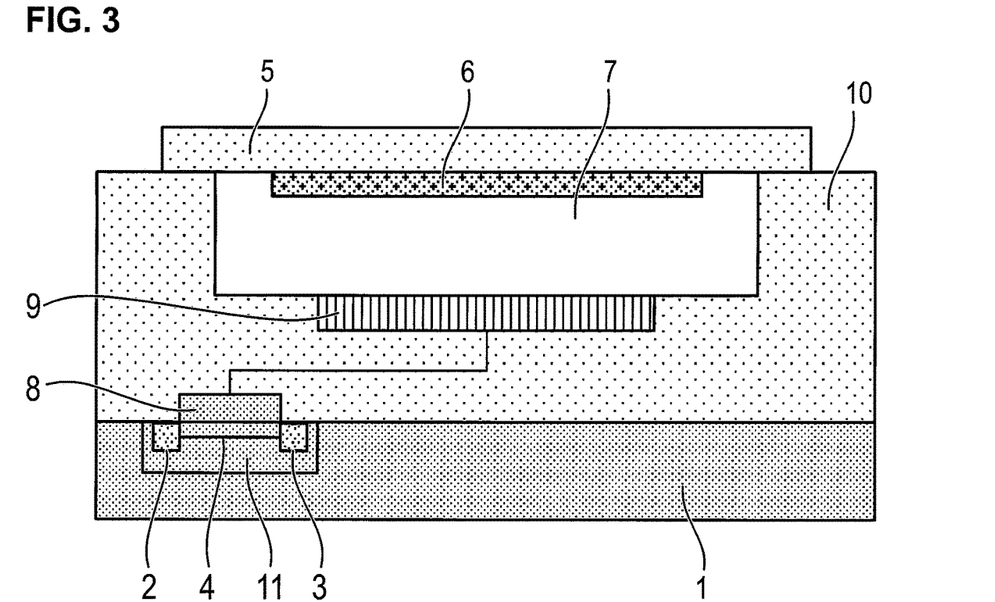
FIG. 3 is a schematic view showing the design of the CCFET sensors according to the present invention.

The design of the CCFET (Capacitive-Coupled Field-Effect Transistor) sensors according to the present invention is explained schematically on the basis of FIG. 3. The channel area 4 is covered with a gate electrode 8 and is arranged within the substrate 1. The gate electrode 8 is connected to the sensor electrode 9 via an electrically conductive connection. The sensor electrode 9 and the receptor layer 6 are separated by the insulation layer 10. The air gap, through which analyte gas flows, is located between the sensor electrode 9 and the receptor layer 6. The substrate consists of pure, undoped silicon (intrinsic silicon) or slightly doped silicon. Embedded in it is a transistor comprising an electrically insulating n-doped trough (substrate 11), in which the drain 2 and source 3, which consist of p-doped silicon and are thus made conductive, are arranged. A channel area 4, which carries, in turn, a p-doped gate 8, is formed in the substrate 11 between the drain 2 and the source 3. This gate 8 is connected, in turn, electrically to a sensor electrode 9 made of noble metal (e.g., platinum or palladium), which is bound in an insulator layer 10. A carrier layer 5 is tightly connected to the insulator layer 10 above the sensor electrode 9. The carrier layer 5 carries a gas-sensitive receptor layer 6 such that an air gap 7 is formed between the receptor layer 6 and the sensor electrode 9. The distance between the receptor layer 6 and the sensor electrode 9 is less than 50 µm, preferably between 5 µm and 20 µm and especially preferably between 10 µm and 12 µm.

If a negative voltage is present at the gate 8 compared to the source 3, the developing electrical field restricts the mobility of the electrons flowing between the drain 2 and the source 3: The channel 4 becomes narrower and the resistance thus becomes greater. This field-effect transistor can be used as a sensor if a variable to be measured—what is of interest here being the concentration of a substance in the air gap—influences a control parameter of the transistor. This control parameter is the potential between the sensor electrode 9 and the receptor layer 6.

If molecules to be detected enter the air gap 7 due to diffusion, they interact with the surfaces 6 and 9. The receptor layer 6 shall ideally interact with the molecules of the substance much more strongly, so that an enrichment of the molecules of the substance will occur at the surface 6. This is achieved by utilizing especially Coulomb forces, i.e., forces acting between positive and negative partial charges.

Figure 4:
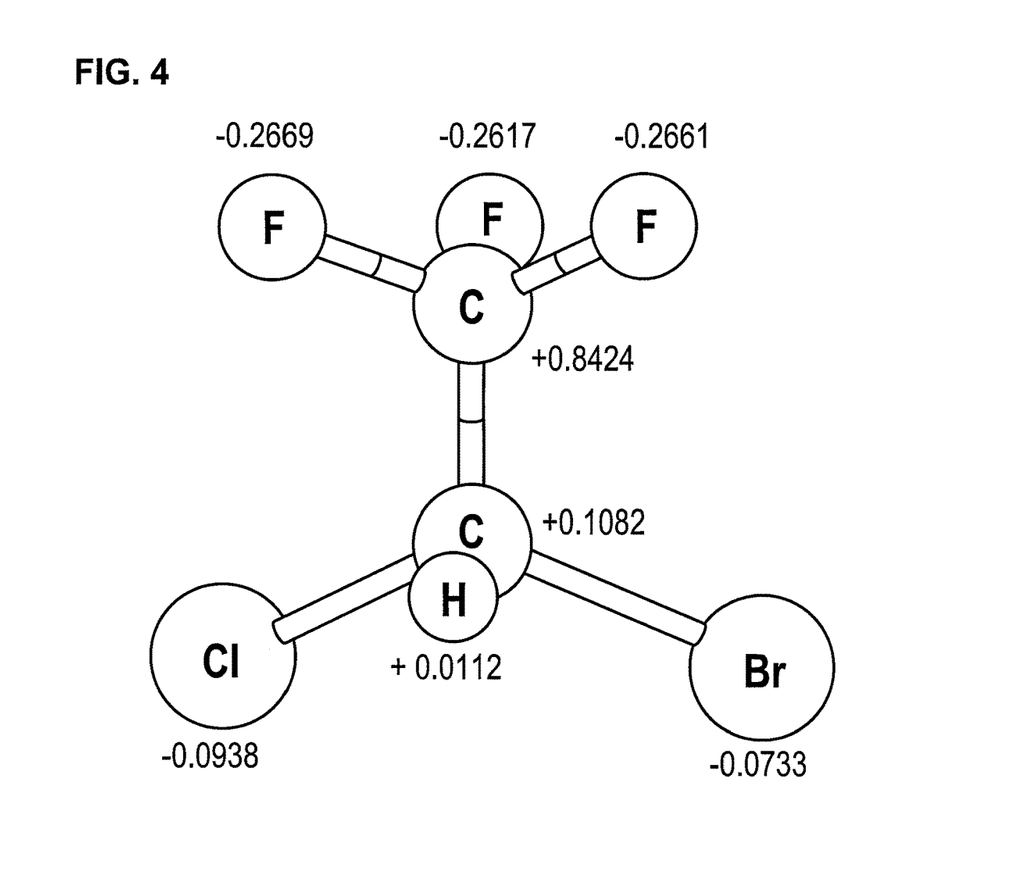
FIG. 4 is a schematic view showing the charge distribution of halothane.

The charge distribution of halothane is shown in FIG. 4. The fluorine atoms carry the greatest part of the negative charge, while the C atom of the trifluoromethyl group carries the positive charge center. The CHBrCl group is neutral relative thereto.

Figure 5:
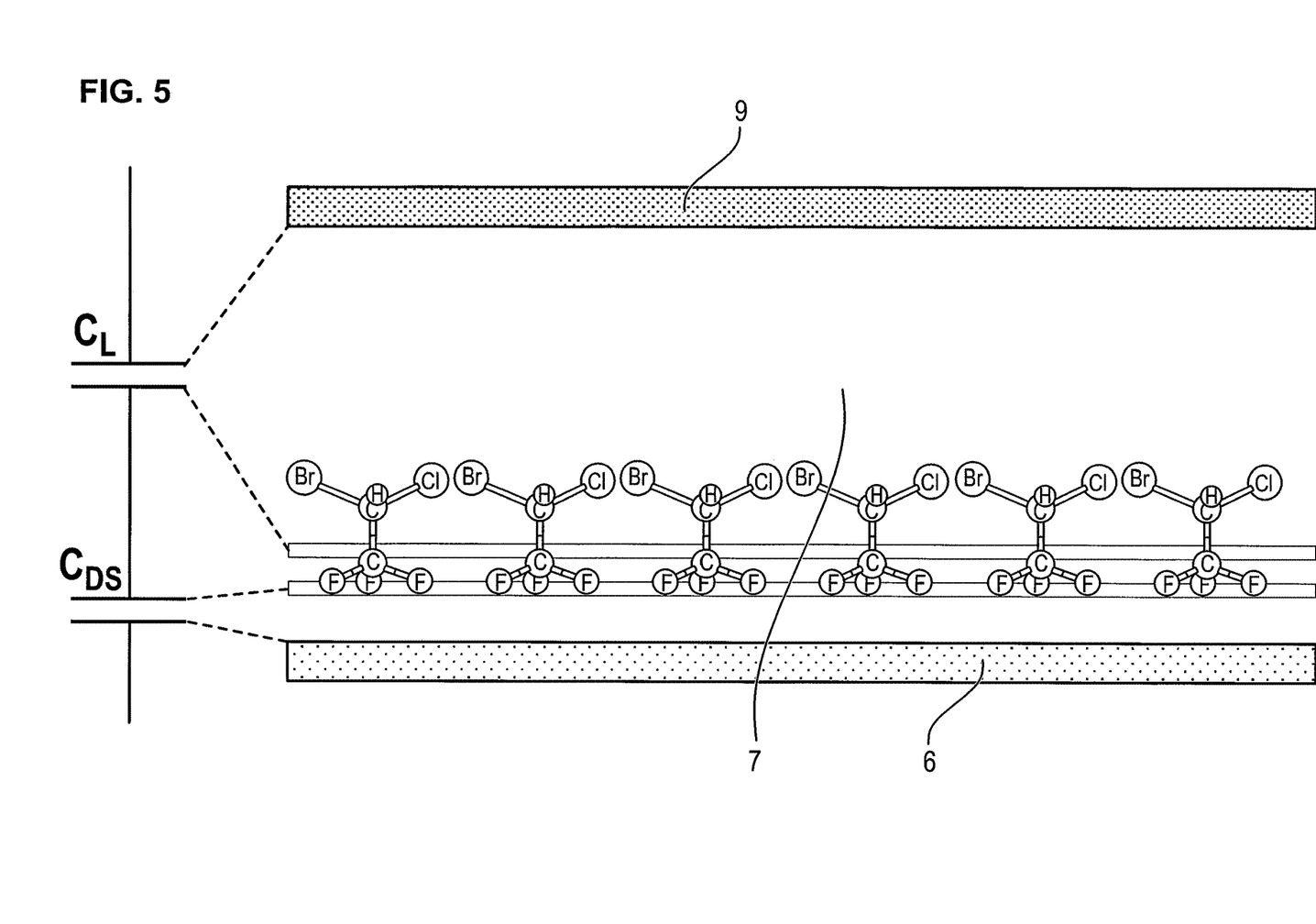
FIG. 5 is a view showing the formation of an electrical double layer by the adsorption of halothane, oriented in the same direction, in a CCFET sensor according to the present invention.

The analyte molecules present in the air gap 7 in FIG. 5 are distributed between the gas phase and the two surfaces 6 and 8. If it is possible to bind the analyte molecules to the surface through a correct configuration of the surface 6 such that they will be arranged oriented in the same direction, i.e., all trifluoromethyl groups in the example of halothane will point away from the sensor electrode 9, an electrical double layer (similar to the Helmholtz double layer in electrochemical sensors) will be formed. This situation can be considered to be a series connection of two capacitors $C_L$ and $C_{DS}$. $C_L$ describes the capacitance over the air layer and $C_{DS}$ the capacitance of the analyte cover and of the receptor layer 6. A total capacitance $C_{tot}$ can be calculated according to $$C_{tot}=C_{DS}*C_L/(C_{DS}+C_L).$$

It is important for the sensor sensitivity that $C_{tot}$ be as low as possible. Since $C_L$ is relatively low due to the distance between the sensor electrode 9 and the analyte double layer, $C_{DS}$ must be selected to be as high as possible.

$C_{DS}$ will become high if (according to $C_{DS}=\varepsilon_0*\varepsilon_r*A/d$, where $\varepsilon_0$ is the electrical field constant of vacuum, $\varepsilon_r$ is the relative permittivity and A is the electrode surface; all three parameters being constant here) the distance d between the analyte double layer and the receptor layer 6 becomes as low as possible. Maximum distances d are reached if analyte molecules are directly adsorbed on the receptor layer 6. Now, d is in the Ångström range.

In addition to the shortest possible distance d, especially the arrangement of the analyte molecules with identical orientation is important in order for the electrical double layer to be able to be formed. This can be ensured by suitable surfaces.

Figure 6:
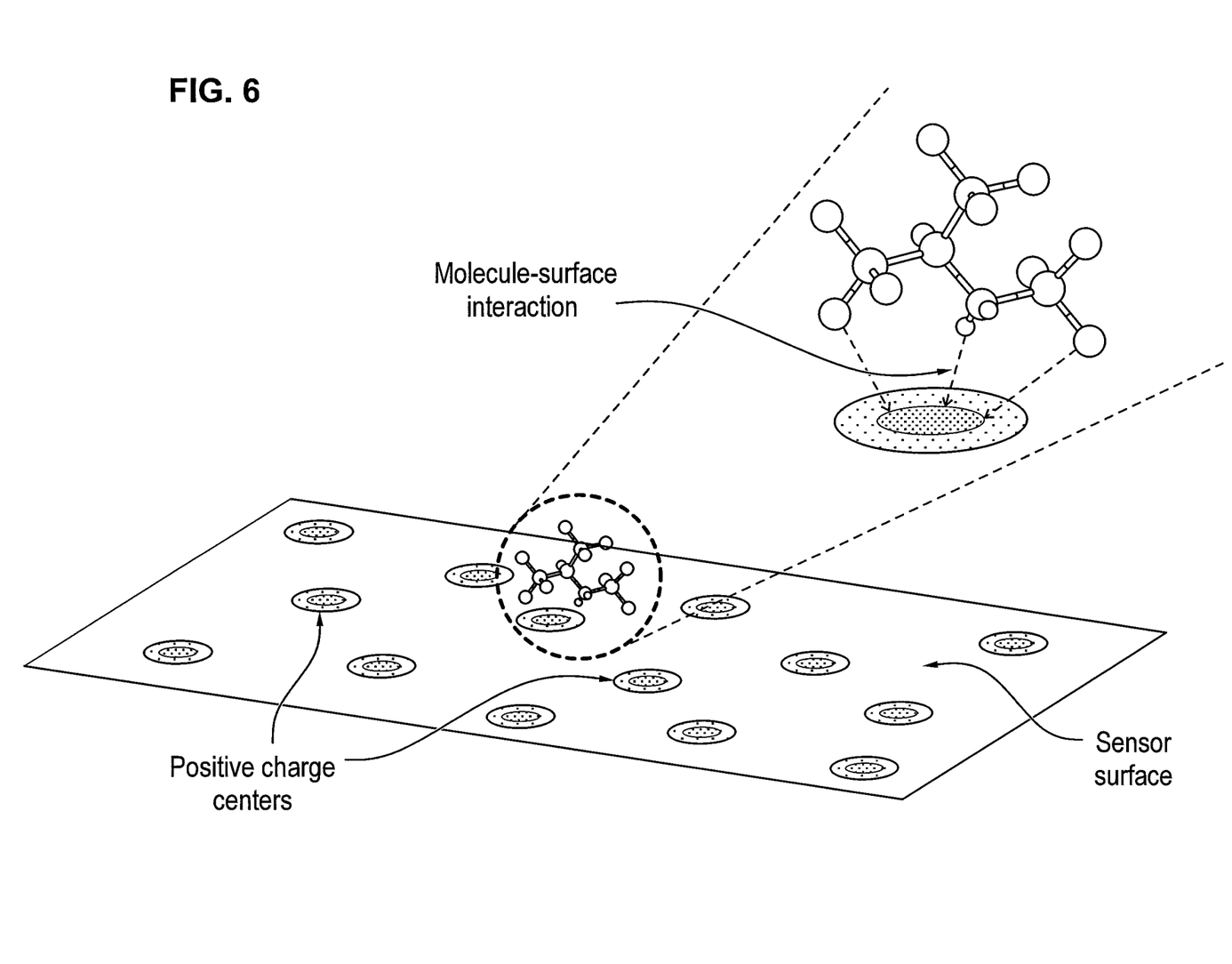
FIG. 6 is a schematic view showing the interaction of sevoflurane with a surface having positive charge centers (with enlargement of the molecular structure)
Figure 7:
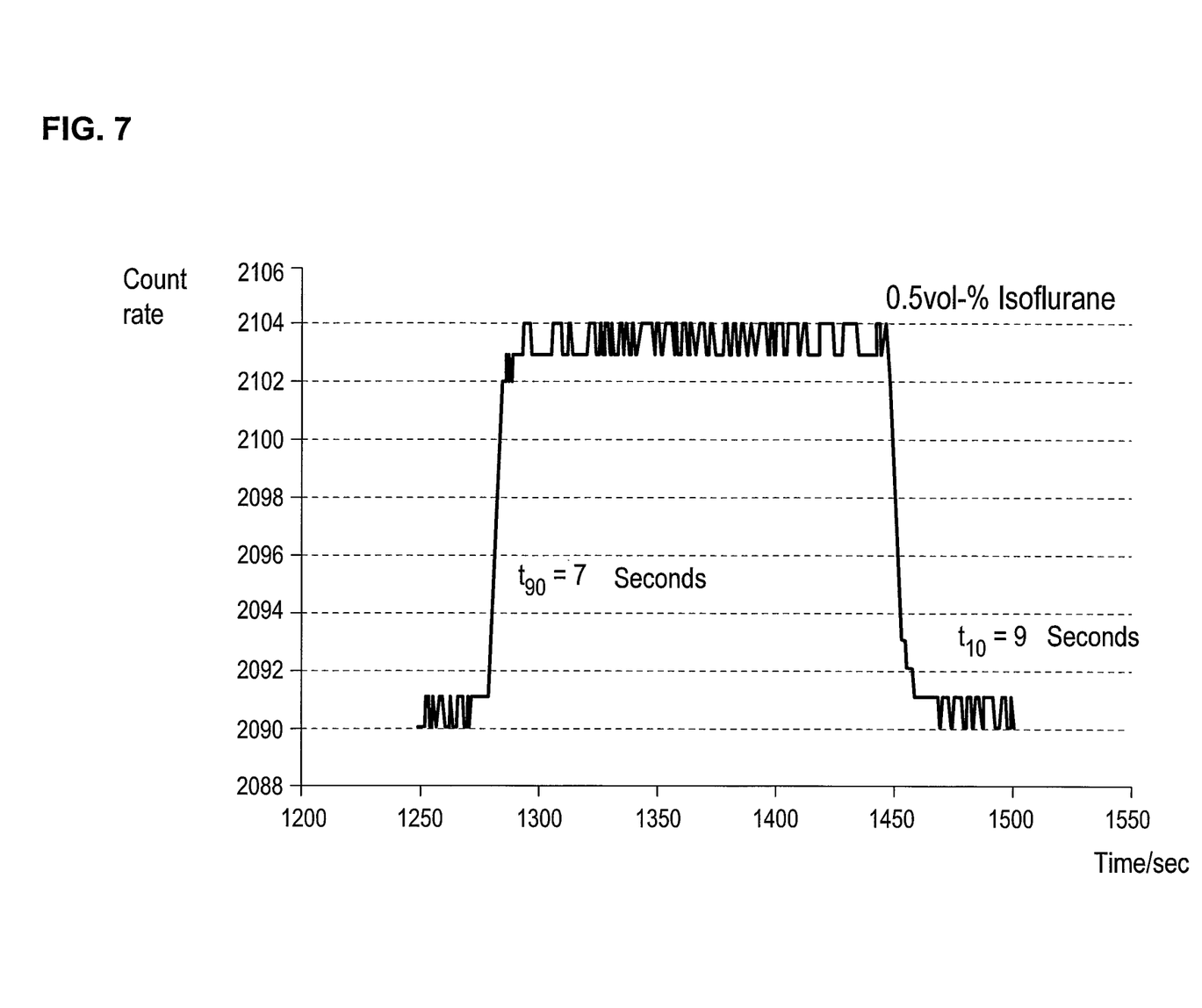
FIG. 7 is a graph showing the response time and the recovery time of a 0.5-vol. % isoflurane signal on a titanium nitride layer.

The analyte-surface interactions that are relevant here are electrostatic interactions. The anesthetics being considered here act as Lewis bases based on their high electron density. This implies the presence of Lewis acids on the surface of the electrode (e.g., FIG. 6) for an effective interaction. A suitable Lewis acid is, for example, the Ti$^+$ cation (formed, e.g., due to a defect in a titanium nitride layer) or also the Cu$^{2+}$ cation in Cu-phthalocyanine surfaces.

A sensor corresponding to FIG. 3, with titanium nitride as the receptor layer 6, reacts, for example, with sevoflurane with a response time of $t_{90}$=7 sec as well as with a recovery time of $t_{10}$=9 sec. The response and recovery times of the other anesthetics are on the same orders of magnitude.

Figure 8:
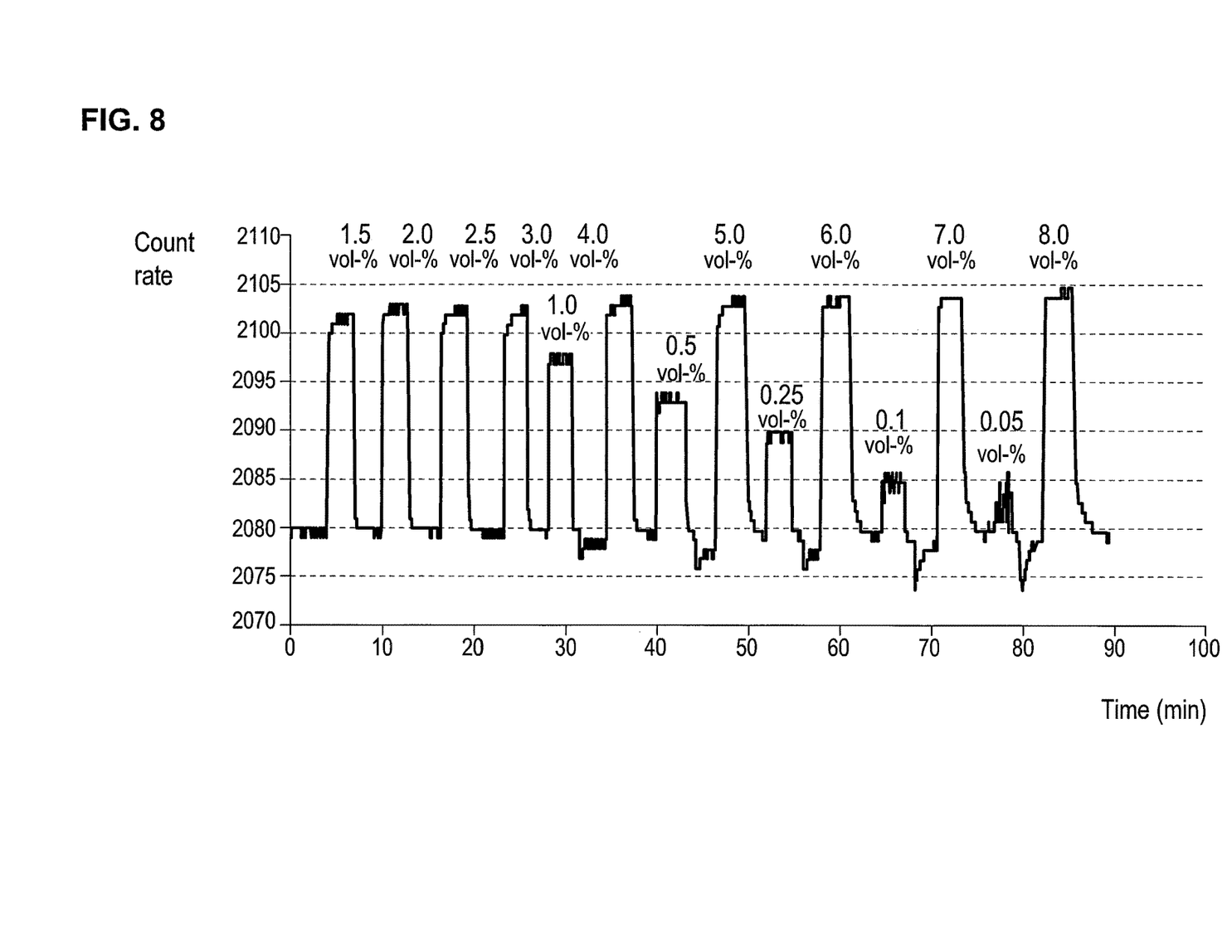
FIG. 8 is a graph showing signals of different sevoflurane concentrations on a titanium nitride layer.

The sensor responses to different concentrations in a range from 0.05 vol. % to 8 vol. % of sevoflurane are shown in FIG. 8.

Figure 9:
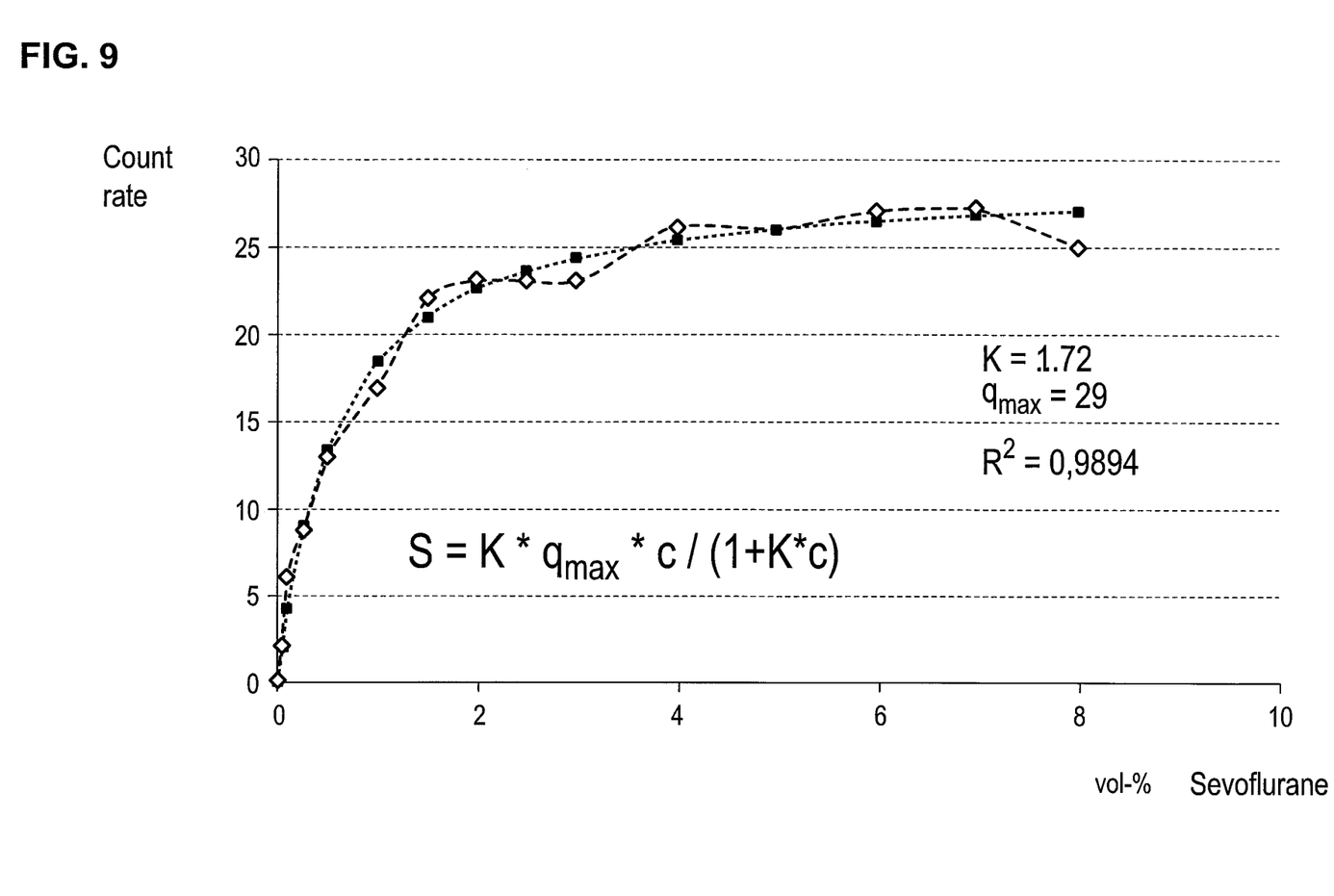
FIG. 9 is a calibration curve of sevoflurane for a CCFET sensor with titanium nitride layer.

The corresponding calibration curve is shown in FIG. 9. It follows the Langmuir function $S=K*q_{max}*c/(1+K*c)$. K is an analyte-specific constant and $q_{max}$ is an indicator of the complete coverage of the surface. All other anesthetic gases follow the Langmuir function as well, but they do so with differences in K and $q_{max}$.

Figure 10:
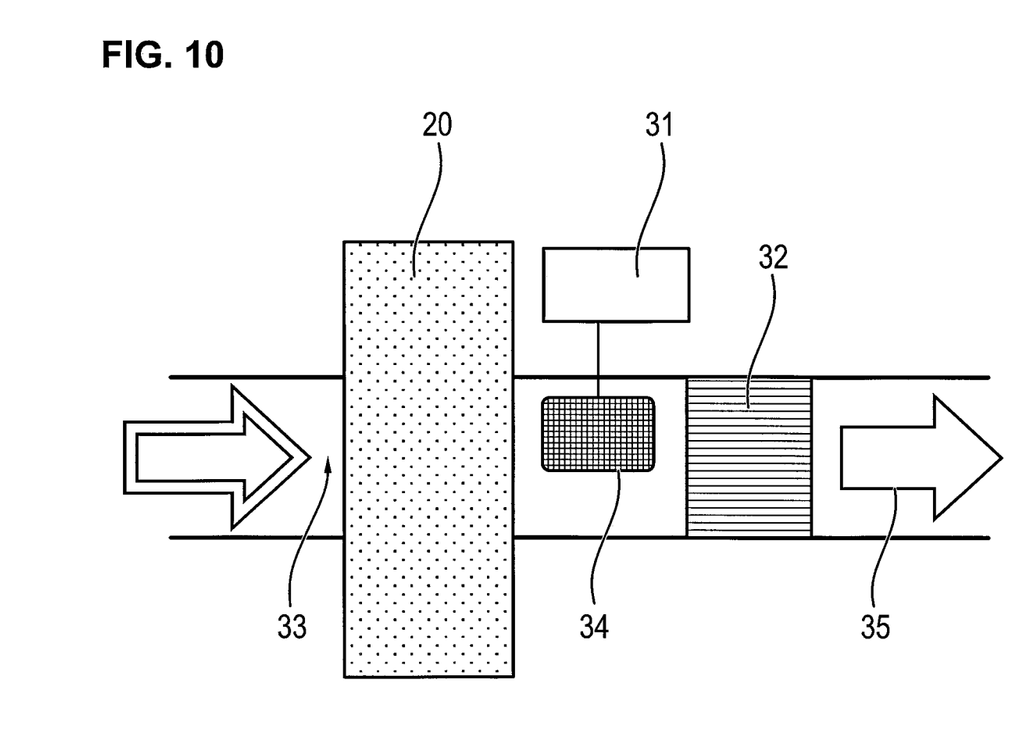
FIG. 10 is a schematic view showing a configuration of a filter depletion indicator with CCFET sensor according to the present invention.

FIG. 10 shows a conceptual design of a filter depletion indicator. The excess air in the closed circuit is sent through the filter. The anesthetic gases are absorbed in the process. At the beginning of the admission to the filter, the sensor detects only the highly volatile carrier gas components flowing through the filter, such as oxygen and possibly laughing gas as well as nitrogen and moisture present in the air. If the absorption capacity of the filter is depleted, the concentration of anesthetic gases rises directly behind the filter, there is a breakthrough through the filter and the anesthetic gas is identified based on the formation of a double layer. The reference number 31 represents the electronic detector, 32 designates the nonreturn valve, reference number 33 designates the outlet of the closed system, 34 designates the CCFET sensor, and the reference number 35 designates the filtered air. The CCFET sensor 34 comprises different CCFET sensors or different CCFET sensor portions in an array (a plural sensor portion/sensor array) with different receptor layers arranged such that anesthetic gas flows through the plurality of gas sensors or sensor portions in parallel gas stream flow portions (portions of the same gas stream flow through two different sensors or sensor portions). The CCFET sensor 34 is an array of at least two sensors having different sensitivities, e.g., on the one hand, a sensor portion has a titanium nitride reception layer containing a percentage of Ti$^+$, and on the other hand a sensor portion has a copper phthalocyanine reception layer containing a percentage of Cu$^{2+}$. These sensors or sensor portions are used simultaneously, i.e., the same gas stream flows through two different sensor portions or sensors of the sensor array 34.

Figure 11:
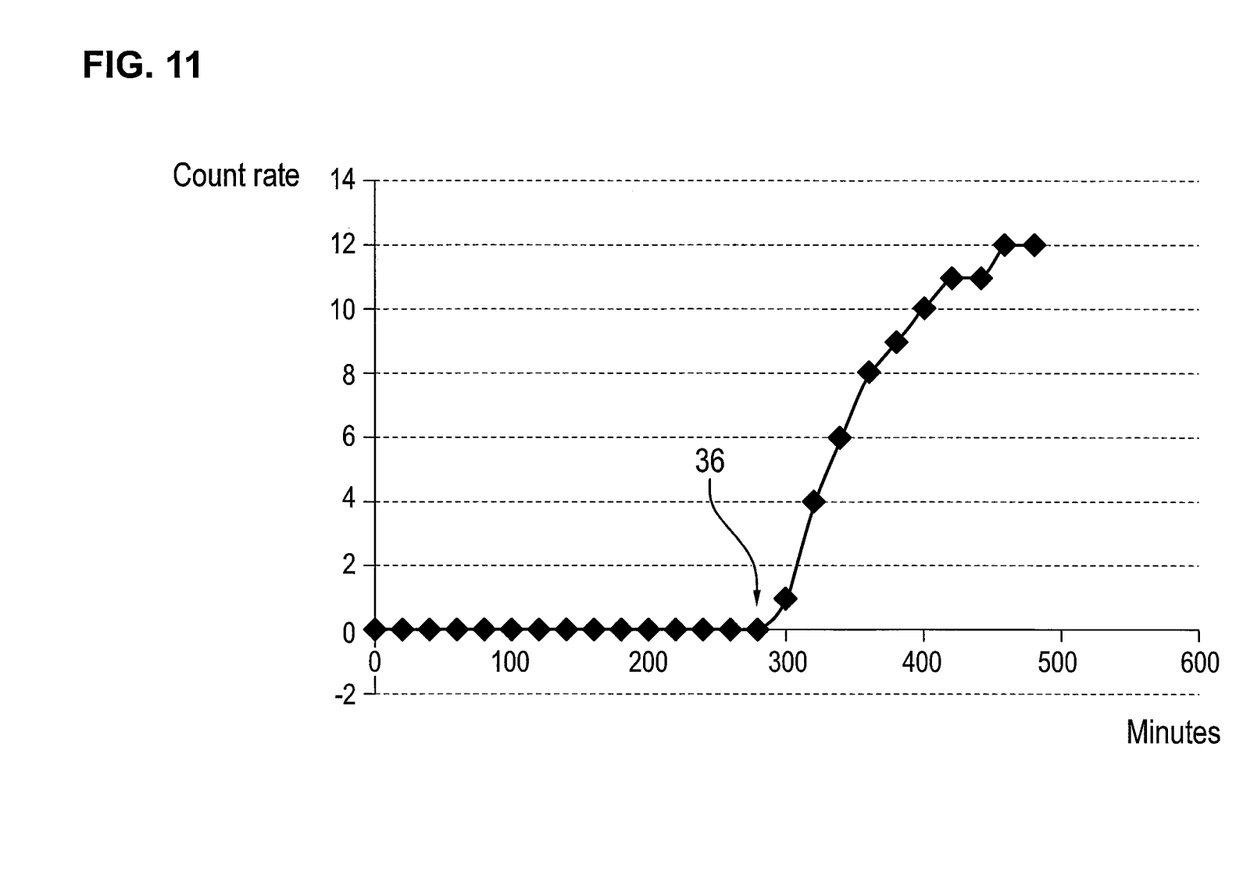
FIG. 11 is a graph showing a detection of a filter breakthrough with a CCFET sensor according to the invention.

FIG. 11 shows a typical breakthrough curve of an anesthesia filter. Reference number 36 designates the filter breakthrough.

While specific embodiments of the invention have been shown and described in detail to illustrate the application of the principles of the invention, it will be understood that the invention may be embodied otherwise without departing from such principles.

What is claimed is:

1. A capacitively coupled field effect transistor gas sensor comprising:
    a first, gas-sensitive, receptor layer with positive charge centers, wherein the first receptor layer is comprised of titanium nitride and titanium+ cations;
    a second, gas-sensitive, receptor layer with positive charge centers, wherein the second receptor layer is comprised of copper phthalocyanine;
    an insulation layer;
    a substrate;

a drain;
a source;
a channel area located between the drain and the source;
a gate electrode; and
a sensor electrode, wherein the channel area is spatially in connection with the gate electrode and at least the drain, the source and the channel area are arranged within the substrate; wherein the gate electrode is connected electrically conductively to the sensor electrode and an air gap is present between the sensor electrode and the first receptor layer, and the sensor electrode and the first receptor layer are otherwise separated by the insulation layer; and wherein the sensor electrode and the first receptor layer are configured such that an analyte gas flows through the air gap, and the analyte gas is an anesthetic gas.

2. A gas sensor in accordance with claim 1, wherein the anesthetic gas is selected from among one or more members of the group comprising desflurane, sevoflurane, isoflurane, enflurane and halothane.

3. A gas sensor in accordance with claim 1, wherein the first receptor layer is configured as an electrically conductive layer and contains pure soft Lewis acids or mixtures of soft Lewis acids and wherein the second receptor layer is configured as an electrically conductive layer and contains pure soft Lewis acids or mixtures of soft Lewis acids.

4. A gas sensor in accordance with claim 3, wherein the soft Lewis acids comprise $Ti^+$, $Ni^{2+}$, $Pd^{2+}$, $Pt^{2+}$, $Cu^+$, $Cu^{2+}$, $Ag^+$, $Au^+$, $Zn^{2+}$, $Cd^{2+}$, $Hg^{2+}$, $In^{3+}$, $Ti^{3+}$, $Ge^{2+}$, $Sn^{2+}$ or $Pb^{2+}$ or any combination of $Ti^+$, $Ni^{2+}$, $Pd^{2+}$, $Pt^{2+}$, $Cu^+$, $Cu^{2+}$, $Ag^+$, $Au^+$, $Zn^{2+}$, $Cd^{2+}$, $Hg^{2+}$, $In^{3+}$, $Ti^{3+}$, $Ge^{2+}$, $Sn^{2+}$ and $Pb^{2+}$.

5. A capacitively coupled field effect transistor gas sensor according to claim 1, wherein:
the first receptor layer is part of a first capacitively coupled field effect transistor sensor portion and the second receptor layer is part of a second capacitively coupled field effect transistor sensor portion;
the first capacitively coupled field effect transistor sensor portion comprises the insulation layer, the substrate, the drain, the source, the channel area located between the drain and the source, the gate electrode and the sensor electrode;
the second capacitively coupled field effect transistor sensor portion comprises a second insulation layer, a second substrate, a second drain, a second source, a second channel area located between the second drain and the second source a second gate electrode and a second sensor electrode; and
the air gap present between the sensor electrode and the first receptor layer is also present between the second sensor electrode and the second receptor layer as a shared air gap whereby the same gas stream flows through two different sensor portions or a second gap is present between the second sensor electrode and the second receptor layer and is arranged such that anesthetic gas flows through the plurality of gas sensor portions in parallel.

6. A capacitively coupled field effect transistor gas sensor according to claim 1, wherein:
the first receptor layer is part of a first capacitively coupled field effect transistor sensor portion and the second receptor layer is part of a second capacitively coupled field effect transistor sensor portion; and
the air gap present between the sensor electrode and the first receptor layer is also present between the sensor electrode and the second receptor layer as a shared air gap whereby the same gas stream flows through two different sensor portions or a second gap is present between the sensor electrode and the second receptor layer and is arranged such that anesthetic gas flows through the plurality of gas sensor portions in parallel.

7. A closed-circuit ventilation system comprising:
a carrier gas source supplying a carrier gas;
an anesthetic gas source supplying for an anesthetic gas; and
a capacitively coupled field effect transistor sensor comprising a first, gas-sensitive, receptor layer with positive charge centers, wherein the first receptor layer is comprised of titanium nitride and titanium+ cations, a second, gas-sensitive, receptor layer with positive charge centers, wherein the second receptor layer is comprised of copper phthalocyanine, an insulation layer, a substrate, a drain, a source, a channel area located between the drain and the source, a gate electrode and a sensor electrode, wherein the channel area is spatially in connection with the gate electrode and at least the drain, the source and the channel area are arranged within the substrate; wherein the gate electrode is connected electrically conductively to the sensor electrode and an air gap is present between the sensor electrode and the first receptor layer, and the sensor electrode and the first receptor layer are otherwise separated by the insulation layer; and wherein the anesthetic gas, as an analyte gas, flows through the air gap.

8. A closed-circuit ventilation system in accordance with claim 7, further comprising a closed ventilation circuit with a patient feed connection wherein the gas sensor is arranged within the closed ventilation circuit of the closed-circuit ventilation system of an anesthesia device to quantitatively determine a concentration of the anesthetic gas as the anesthetic gas is being fed to a patient.

9. A closed-circuit ventilation system in accordance with claim 8, wherein the closed ventilation circuit comprises an outlet for the discharge the carrier gas and anesthetic gas and an anesthetic gas filter, wherein the anesthetic gas is sent at the outlet through the anesthetic gas filter and the gas sensor is arranged downstream of the anesthetic gas filter.

10. A closed-circuit ventilation system in accordance with claim 9, further comprising a filter depletion indicator with an electronic detector, which indicates that the anesthetic gas filter is to be replaced when a defined threshold value is reached.

11. A closed-circuit ventilation system in accordance with claim 9, wherein the closed ventilation circuit further comprises a nonreturn valve wherein the gas sensor is arranged between the anesthetic gas filter and the nonreturn valve.

12. A closed-circuit ventilation system in accordance with claim 7, wherein:
the first receptor layer is part of a first capacitively coupled field effect transistor sensor portion and the second receptor layer is part of a second capacitively coupled field effect transistor sensor portion;
the first capacitively coupled field effect transistor sensor portion comprises the insulation layer, the substrate, the drain, the source, the channel area located between the drain and the source, the gate electrode and the sensor electrode;
the second capacitively coupled field effect transistor sensor portion comprises a second insulation layer, a second substrate, a second drain, a second source, a second channel area located between the second drain and the second source, a second gate electrode and a second sensor electrode;

the air gap present between the sensor electrode and the first receptor layer is also present between the second sensor electrode and the second receptor layer as a shared air gap whereby the same gas stream flows through two different sensor portions or a second gap is present between the second sensor electrode and the second receptor layer and is arranged such that anesthetic gas flows through the plurality of gas sensor portions in parallel.

13. A closed-circuit ventilation system in accordance with claim 7, wherein the gas sensor further comprises a heating element or is surrounded by a heating element to heat the first receptor layer or to heat the first receptor layer and the sensor electrode prior to a measurement or to heat the first receptor layer or to heat the first receptor layer and the sensor electrode for regeneration between two measurements.

14. A closed-circuit ventilation system in accordance with claim 13, wherein the heating element heats first the receptor layer or heats the first receptor layer and the sensor electrode for a time $\Delta t_H$ of 10 sec to 10 minutes to a temperature T of 60° C. to 120° C.

15. A closed-circuit ventilation system in accordance with claim 7, wherein the first receptor layer is configured as an electrically conductive layer and contains pure soft Lewis acids or mixtures of soft Lewis acids and wherein the second receptor layer is configured as an electrically conductive layer and contains pure soft Lewis acids or mixtures of soft Lewis acids.

16. A closed-circuit ventilation system in accordance with claim 15, wherein the soft Lewis acids comprise $Ti^+$, $Ni^{2+}$, $Pd^{2+}$, $Pt^{2+}$, $Cu^+$, $Cu^{2+}$, $Ag^+$, $Au^+$, $Zn^{2+}$, $Cd^{2+}$, $Hg^{2+}$, $In^{3+}$, $Ti^{3+}$, $Ge^{2+}$, $Sn^{2+}$ or $Pb^{2+}$ or any combination of $Ti^+$, $Ni^{2+}$, $Pd^{2+}$, $Pt^{2+}$, $Cu^+$, $Cu^{2+}$, $Ag^+$, $Au^+$, $Zn^{2+}$, $Cd^{2+}$, $Hg^{2+}$, $In^{3+}$, $Ti^{3+}$, $Ge^{2+}$, $Sn^{2+}$ and $Pb^{2+}$.

17. A closed-circuit ventilation system in accordance with claim 7, wherein:
the first receptor layer is part of a first capacitively coupled field effect transistor sensor portion and the second receptor layer is part of a second capacitively coupled field effect transistor sensor portion; and
the air gap present between the sensor electrode and the first receptor layer is also present between the sensor electrode and the second receptor layer as a shared air gap whereby the same gas stream flows through two different sensor portions or a second gap is present between the sensor electrode and the second receptor layer and is arranged such that anesthetic gas flows through the plurality of gas sensor portions in parallel.

18. A method for a quantitative determination of at least one anesthetic gas, the method comprising the steps of:
providing a ventilation system comprising a carrier gas source supplying a carrier gas, an anesthetic gas source supplying an anesthetic gas and a capacitively coupled field effect transistor sensor comprising a first, gas-sensitive, receptor layer with positive charge centers, wherein the first receptor layer is comprised of titanium nitride and titanium+ cations, a second, gas-sensitive, receptor layer with positive charge centers, wherein the second receptor layer is comprised of copper phthalocyanine, an insulation layer, a substrate, a drain, a source, a channel area located between the drain and the source, a gate electrode and a sensor electrode, wherein the channel area is spatially in connection with the gate electrode and at least the drain, the source and the channel area are arranged within the substrate; wherein the gate electrode is connected electrically conductively to the sensor electrode and an air gap is present between the sensor electrode and the first receptor layer, and the sensor electrode and the first receptor layer are otherwise separated by the insulation layer;

providing a flow of an analyte gas, comprising the anesthetic gas, through the air gap; and determining quantitatively the anesthetic gas.

19. A method according to claim 18, wherein the anesthetic gas is desflurane, sevoflurane, isoflurane, enflurane or halothane or any combination of desflurane, sevoflurane, isoflurane, enflurane and halothane.

20. A method according to claim 18, wherein:
the first receptor layer is part of a first capacitively coupled field effect transistor sensor portion and the second receptor layer is part of a second capacitively coupled field effect transistor sensor portion;

the first capacitively coupled field effect transistor sensor portion comprises the insulation layer, the substrate, the drain, the source, the channel area located between the drain and the source, the gate electrode and the sensor electrode;

the second capacitively coupled field effect transistor sensor portion comprises a second insulation layer, a second substrate, a second drain, a second source, a second channel area located between the second drain and the second source a second gate electrode and a second sensor electrode; and the air gap present between the sensor electrode and the first receptor layer is also present between the second sensor electrode and the second receptor layer as a shared air gap, whereby the same gas stream flows through two different sensor portions, or a second gap is present between the second sensor electrode and the second receptor layer and is arranged such that anesthetic gas flows through the plurality of gas sensor portions in parallel.

* * * * *